United States Patent [19]

Haga et al.

[11] Patent Number: 4,510,243

[45] Date of Patent: Apr. 9, 1985

[54] ANAEROBIC DIGESTION PROCESS OF WASTES CONTAINING CELLULOSE

[75] Inventors: Ryoichi Haga; Masahiko Ishida; Yoji Odawara, all of Hitachi, Japan

[73] Assignee: The Agency of Industrial Science and Technology, Tokyo, Japan

[21] Appl. No.: 434,321

[22] Filed: Oct. 14, 1982

[30] Foreign Application Priority Data

Oct. 14, 1981 [JP] Japan .................................. 56-162628

[51] Int. Cl.$^3$ .......................... C12P 5/02; C12N 1/22; C02F 3/30; C02F 11/04
[52] U.S. Cl. .................................. 435/167; 435/139; 435/140; 435/141; 435/801; 435/291; 435/822; 435/252; 210/605; 210/611; 210/613; 210/614; 210/630
[58] Field of Search ................................ 435/139–141, 435/167, 801, 163, 165, 252; 210/605, 611, 613, 614, 630

[56] References Cited

U.S. PATENT DOCUMENTS

| 3,241,943 | 3/1966 | Bystrom | 435/167 X |
| 4,022,665 | 5/1977 | Ghosh et al. | 435/167 |
| 4,213,857 | 7/1980 | Ishida et al. | 210/612 X |

*Primary Examiner*—Lionel M. Shapiro
*Attorney, Agent, or Firm*—Birch, Stewart, Kolasch and Birch

[57] ABSTRACT

The present invention relates to an anaerobic digestion process of wastes containing cellulose, in which, after liquefying by bringing wastes containing cellulose in slurry state into contact with facultative anaerobic bacteria with pH adjusted between 6.5–8.0 and oxidation-reduction potential controlled between −50–300 mV with oxygen supply, the liquefied slurry is then converted into methane and carbon dioxide by bringing it into contact with obligatory anaerobic bacteria to recover methane efficiently.

4 Claims, 6 Drawing Figures

ANAEROBIC DIGESTION PROCESS OF WASTES CONTAINING CELLULOSE

BACKGROUND OF THE INVENTION

1. Field of the Invention

The present invention relates to an anaerobic digestion process of wastes containing cellulose, specifically an anaerobic digestion process of wastes containing cellulose suitable for liquifactive fermentation by converting efficiently cellulose contained in wastes into volatile fatty acids and for recovering methane after liquefactive fermentation.

2. Description of the Prior Art

Massive quantity of wastes containing cellulose is discharged every year from food processing industries, paper manufacturing industries or lumber industries, including agricultural wastes and livestock wastes, municipal wastes, etc. A part of those wastes are utilized as material for composts, but almost all the rest of the wastes are finally disposed by means of incinerating, landfilling, etc. These means of disposing, however, cause secondary pollution and have problems such as tightened legal restrictions or increasing disposal cost.

Recently, research has been carried out to develop an anaerobic digestion process to dispose of municipal waste in Japan and in the United States.

This anaerobic digestion is a process to convert high-polymeric organic matter such as saccharide, protein or fat into methane and carbon dioxide by the fermenting effect of anaerobic bacteria, consisting mainly of two reactions, i.e., liquefaction in which organic matter such as saccharide, protein, fat, etc., become volatile fatty acids of acetic acid, propionic acid or lactic acid by the action of facultative anaerobic bacteria (which will be hereinafter referred to as "liquefying bacteria") and gasification in which volatile fatty acids produced in the above process are converted into methane by obligatory anaerobic bacteria (which will be referred to as "gasifying bacteria" hereinafter).

When the anaerobic digestion process like this is carried out by a one-step disposal process, a very small amount of bacteria of Cellulomonas or Clostridium which dissimilate cellulose exist in an anaerobic digester, and a part of the cellulose is decomposed, but the speed of decomposition is much slower than that of organic matter which is easy to decompose such as saccharide or protein and is exhausted out of the system before it is changed into methane.

Applicants previously proposed a two-step disposal process in which two reactions of liquefaction and gasification are carried out separately. (U.S. Pat. No. 4,213,857: "Anaerobic Digestion Process", patented on July 22, 1980, M. Ishida et al). By adopting this process, liquefaction and gasification can be carried out separately under the most preferable condition for each of the two reactions.

As a result, time required for disposal can be reduced and this process has a great effect on disposing such wastes as municipal wastes which mainly consists of protein or starches.

However, cellulose is hardly liquefied in a condition favorable for liquefying such decomposable elements as saccharide, protein, fats by the two-step digestion process.

Furthermore, the operation of an anaerobic digestion system for organic matter is generally dependent on past experience. Degrees of digestion have been judged by measuring quantity of generated gas, methane concentration, pH of digested slurry, alkalinity, organic acid concentration, and oxidation-reduction potential of organic matter put into the equipment.

Among these items to be measured, the oxidation-reduction potential has been controlled to be under $-500$ mV from the empirical viewpoint that digesting efficiency decreases in higher potential than $-500$ mV, but wastes containing cellulose cannot be sufficiently liquefied in such an operating condition.

On the other hand, liquefying bacteria (facultative anaerobic bacteria) is a group of bacteria being able to grow where oxygen exits, but gasifying bacteria (obligatory anaerobic bacteria) is a group of bacteria which die in the atmosphere containing oxygen (aerobic condition). Accordingly, there is a big difference between the tolerance to oxygen of liquefying bacteria and that of gasifying bacteria.

For the above reason, it is desirable to give priority to the growth of liquefying bacteria by bringing the wastes into contact with oxygen and suppressing the growth of gasifying bacteria. Actually, however, a stable liquefactive effect has not been obtained.

SUMMARY OF THE INVENTION

The first object of the present invention is to offer an anaerobic digestion process for the effective liquefying fermentaton of wastes containing cellulose, which can convert cellulose in wastes into volatile fatty acid.

The second object of the invention is to offer an anaerobic digestion process to effectively liquefy and ferment wastes containing cellulose, and then to recover methane by gasification.

After re-examining an anaerobic digestion of wastes containing cellulose, it has been found that cellulose is hardly liquefied under the condition where an easily decomparable element such as saccharide, protein or fat is easily liquefied by decomposition and that there is a need to develop a more favorable condition for decomposing cellulose. Furthermore, the inventors have determined that, in an anaerobic digestion, the two-step digestion of liquefaction and gasification is difficult to adopt with use of only the difference of the most favorable pH value of each reaction, as is adopted for municipal wastes.

The present invention was obtained from first adjusting pH of the wastes containing cellulose in a slurry state between 6.5–8.0, controlling the oxidation-reduction potential between $-50$—$-300$ mV with an oxygen supply, bringing the wastes into contact with facultative anaerobic bacteria for the purpose of liquefactive fermentation, and secondly converting the obtained slurry into methane and carbon dioxide after the above process of liquefactive fermentaion by bringing it into contact with obligatory anaerobic bacteria and then separating the obtained digested slurry into separate water and digested sludge.

However, facultative anaerobic bacteria (liquefying bacteria) coexists ordinally with obligative anaerobic bacteria (gasifying bacteria). Accordingly, it is effective to stop or suppress temporarily the activity of gasifying bacteria in order to fully display the activity of liquefying bacteria. For example, if the pH of the slurry is decreased temporarily to between 5.0 and 6.0, the activity of gasifying bacteria is stopped or suppressed. As a result, the activity of liquefying bacteria is predominant in this slurry. After that, if the pH of the slurry increases again to between 6.5 and 8.0, only the activity of liquefying bacteria becomes active. However, if the pH of this slurry increases from low to high as it is, the activity of gasifying bacteria becomes active again. So, it is desirable to control the oxidation-reduction potential between −50 mV and −500 mV in the course of this step. If the oxidation-reduction potential holds in this region, the increase of the gasifying bacteria is suppressed. As described above, if the pH of the slurry passes through this low pH region, the action of gasifying and liquefying bacteria is carried out effectively separately.

BRIEF DESCRIPTION OF THE DRAWINGS

The present invention will be fully explained in detail referring now, by way of example, to the accompanying drawings, in which.

DESCRIPTION OF THE PREFERRED EMBODIMENT

Figure 1:
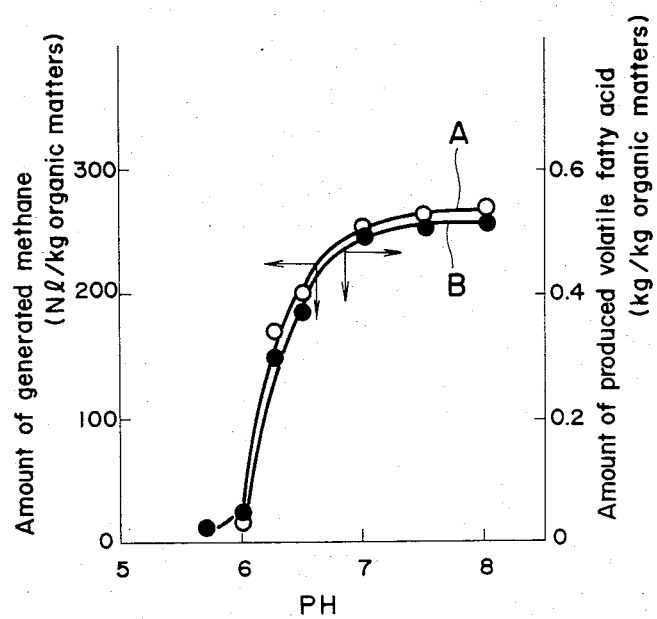
FIG. 1 is a diagram showing the relation between pH and quantities of generated methane and produced volatile fatty acid in the anaerobic digestion of cellulosic materials.

FIG. 1 shows the relation of the amount of volatile fatty acids (B) produced in liquefaction of cellulosic materials and generated amount of methane (A) to pH. It is known from the diagram that dependence on pH of the amount of volatile fatty acids and that of the generated amount of methane in liquefaction of cellulose are nearly equivalent to each other. Accordingly, in liquefaction of cellulose, it is impossible to carry out liquefaction and gasification using only the difference of the optimum pH as efficiently as in disposing of kitchen garbage.

According to the invention, liquefactive fermentation of cellulose is performed in the range of pH 6.5–8.0. Outside this range of pH, the production of volatile fatty acids extraordinarily and unexpectedly decreases. Moreover, during the time of liquefactive fermentation of cellulose, the oxidation-reduction potential is controlled at −50 − −300 mV. Liquefactive fermentation of cellulose proceeds efficiently at a low reduction range below −50 mV, and the concentration of volatile fatty acids drops when oxidation-reduction potential is below −250 mV, particularly below −300 mV. This is caused by conversion of volatile fatty acids to methane in gasification.

The preferred embodiment of the invention will be described hereinafter referring to the attached flow sheets.

Figure 2:
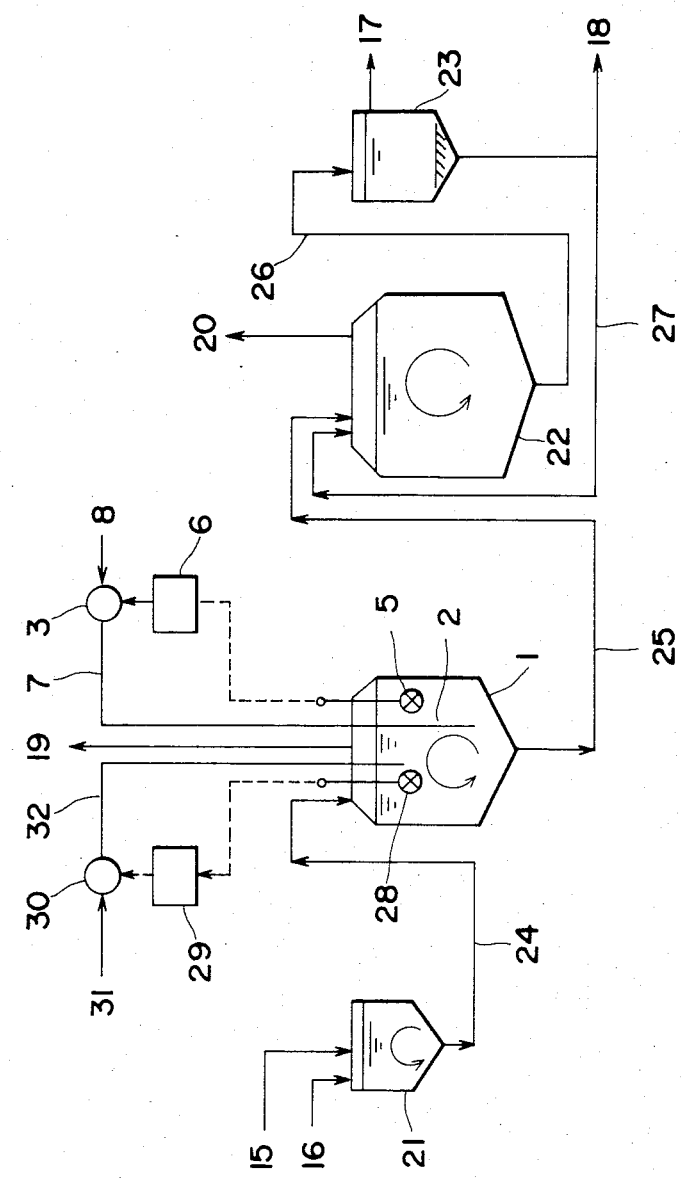
FIG. 2 is a flow chart of one of the embodiments of the invention.

In FIG. 2, preferable waste containing cellulose is one which contains less than 100% of cellulose, less than 10% of plastics, less than 10% of glass, chinaware fragments and pebbles, and less than 0.5% of metal fragments by dry goods standard.

The above waste containing cellulose 15 and water 16 are put into a slurry tank 21 to be made into slurry.

When large solid matter is mixed in the wastes containing cellulose, it is better to crush the waste before making it into a slurry for preventing trouble with the apparatus and for improving disposal efficiency.

For the same reason, it is desirable to remove inorganic matter, such as glass, chinaware fragments, pebbles, metal fragments, etc., deposited on the bottom of the slurry tank.

Water to be used for making the slurry is not restricted to a particular sort, but any of service water, sewage, sewage sludge, water from secondary treated activated sludge, tap water in anaerobic digestion, etc. is usable. When waste containing cellulose contains enough water and is already fluidized, there is no need to add water to it.

When properties of the slurry are not suitable for survival of bacteria which affect anaerobic digestion, it is desirable to adjust them in the slurry tank 21. It is further desirable to adjust C/N balance and nutritive elements for carrying out favorable anaerobic digestion. After being made into slurry, wastes (containing cellulose) are transferred through the transfer tube 24 into the liquefaction tank 1, where they are kept at a definite temperature in contact with liquefying bacteria while being stirred for several days. During this process, organic matter such as cellulose are decomposed into low molecules and further are converted into volatile fatty acids. During this liquefying process, oxygen is blown in while the pH is controlled between 6.5–8.0 in order to carry out liquefaction only and suppress the process of gasification. More specifically, oxygen is blown into the slurry through the oxygen supply tube 7 by driving an oxygen supply pump 3 with oxidation-reduction potential controller 6 connected with oxidation-reduction potential measuring electrode 5 soaked in the slurry, and the oxidation-reduction potential being kept at −50 − −300 mV. Gasification is suppressed by this process, and no methane is recognized in the gas 19 generated by liquefactive fermentation. Moreover, as volatile fatty acids are stored in slurry with the liquefactive fermentation in this liquefying process, the pH of the slurry foam decreases and causes liquefaction to stop. For preventing this stop of liquefaction, a process to maintain definite pH is indispensable. For this purpose, neutralizer 31 is mixed into the slurry when the pH decreases, through the neutralizer supply tube 32 with the neutralizer supply pump 30 being driven by the pH controller 29 which has a pH measuring electrode set in the fermented slurry, and thus the pH is maintained between 6.5–8.0.

As liquefying bacteria, Clostridium, Bacillus, Staphylococcus, Luminococcus, Bacteroides, Butylivibrio, Proteus, Bacterium, Cellulomonas are usable. Generally, one or a mixture of more than two of these bacteria is utilized.

The oxygen to be supplied into the fermenting slurry to control oxidation-reduction potential is not specifically restricted, but air or pure oxygen can be used. As a neutralizer to control pH, any of NaOH, KOH, $Na_2CO_3$, $Ca(OH)_2$, $CaCO_3$ is adaptable. It is desirable to maintain the temperature of the slurry in the range of 30°–60° C. during the liquefying process. As a method to stir the slurry in the liquefaction tank 1, any of the conventional gas stirring methods, mechanically stirring methods and slurry injecting methods is adoptable. As a method to maintain a definite temperature of the slurry, any of the well known methods of steam injecting method, hot-water jacket method, heat exchange method, etc. can be used.

Though the gas 19 produced during the liquefying process varies depending on the quality of the materials, its major components ae generally $CO_2$ 50–80% and $H_2$ 20–50% including a little quantity of $H_2S$. With the use of air as the oxygen source for controlling the oxidation-reduction potential, $N_2$ and unused $O_2$ dilute the gas of the above composition. Also, the gas is diluted by unused $O_2$ when pure oxygen is used as oxygen source.

Means to supply oxygen into the fermentation slurry is not restricted to any particular source, and any conventional means corresponding to the stirring method of liquefaction tank can be employed.

The slurry after the liquefying process is put into the gasification tank 22 through the transfer tube 25, and the volatile fatty acid is converted to methane and carbon dioxide by the effect of the gasifying bacteria. In order to carry out this gasification efficiently, it is required to adjust the slurry to a pH of between 7 and 8 by heating it to a temperature of between 30° to 60° C. while sufficiently stirring under an anaerobic atmosphere. The heating and stirring methods can be practiced by the same methods as those adopted in the above liquefying process. The pH is controlled by adding hydrochloric acid or an organic acid. Conventionally, Methanosarcina, Methanococcus, Methanobacterium, etc. are usable as gasifying bacteria.

Gas 20 produced in this gasifying fermentation contains 55–90% of $CH_4$ and 10–40% of $CO_2$ as its major components and also a very small amount of $H_2S$, $N_2$ and $H_2$. This gasifying fermentation gas is utilized as a heat source for maintaining the temperature of the apparatus and energy source for stirring.

The slurry (digested slurry) produced through gasifying fermentation is introduced into a solid-liquid separator 23 through transfer tube 26, and it is separated into separate water 17 and digested sludge 18. The separate water 17 is exhausted after removing BOD by secondary treatment of activated sludge disposing process. A part of digested sludge 18 is returned to the gasification tank 22 through the transfer tube 27 to raise the sludge concentration of the gasification tank. The surplus digested sludge is dehydrated and dried to be utilized as an organic fertilizer.

Figure 3:
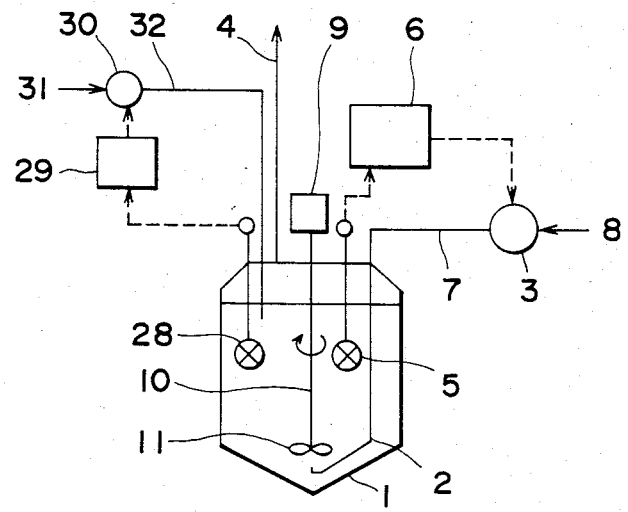
FIG. 3 and FIG. 4 are outline charts showing alternative embodiments of a liquefaction tank of the invention.

FIG. 3 is a typical diagram of a supplying method of oxygen in the liquefaction tank 1. In FIG. 3, the oxidation-reduction potential of the liquefied and fermented slurry is measured with oxidation-reduction potential measuring electrode 5 which is soaked in the slurry and immediately compared with the set value by oxidation-reduction potential controller 6. When the measured value is lower than the set value, oxygen is supplied into the slurry by oxygen supply pump 3 through oxygen supply tube 7 and oxygen blowing tube 2. It is desirable to discharge oxygen into the slurry directly under the stirring wings. Air bubbles are pulverized by the shearing effect produced by the rotary stirring wings, and the gas-liquid contact efficiency between oxygen and slurry is improved. As a result, improved responding speed and reduced quantity of blown-in oxygen are obtained. When sufficient pressure is provided for the oxygen source 8 to be blown into the slurry, the oxygen supply pump 3 can be omitted by adopting an automatic switch valve.

Figure 4:
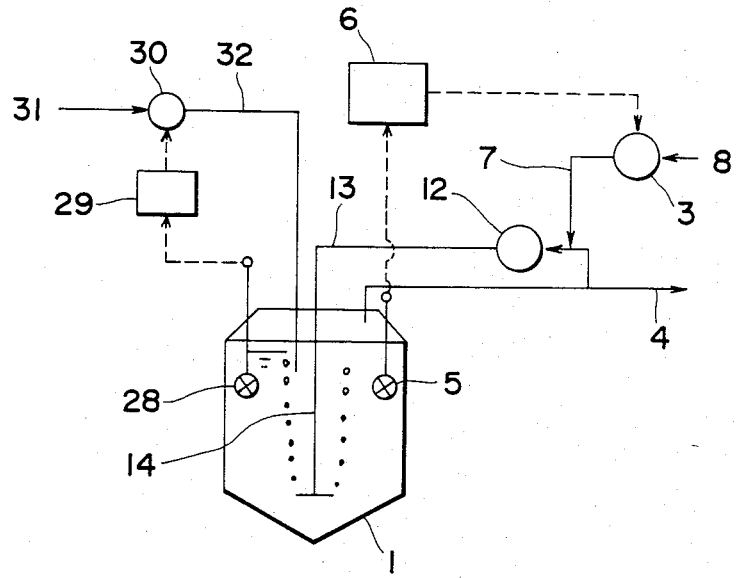

FIG. 4 typically shows an alternative plan of oxygen supplying method to the liquefaction tank 1. Referring to FIG. 4, when the measured value of oxidation-reduction potential is lower than its set value, oxygen is supplied into the slurry as with the mechanical stirring method in FIG. 3, through oxygen supply tube 7, stirring gas supply pump 12 and stirring gas supply tube 13 by driving oxygen supply pump 3. Oxygen supplied into the slurry ascends through the slurry and circulates through a part of surplus gas exhaust tube 4, stirring gas supply pump 12 and stirring gas supply tube 13 successively, and is used repeatedly. Accordingly, the utility factor of oxygen is high. When the oxygen source 8 is given sufficient pressure to be blown into the slurry, an automatic switch valve can be utilized in place of the oxygen supply pump.

PREFERRED EMBODIMENTS

Embodiment 1

Municipal wastes gathered without assorting are pulverized into 30 mm particles, and fractions which highly contain paper 0.07 kg (water content 60%, dry goods standard paper 57%, kitchen refusal 19%, wood fragments 8%, plastics 10%, metals 3%, glass and chinaware fragments and pebbles 3%) and water 0.33 kg is mixed to make slurry. Next, the said slurry is put together with 1.6 kg of seeds into fermenting tank with inner volume of 2.6 l having a stirrer, a pH controller, an oxidation-reduction potential controller and a hot-water jacket. Then, batch type anaerobic digestion test was carried out at 50 rpm, pH 7.0 and 60° C. with oxidation-reduction potential controlled at +100--−600 mV by air blowing. As added liquefying germs mixed liquefaction bacteria such as Clostridium, Bacillus, Staphylococcus, Luminococcus, Bacteroides, Butylivibrio, Eubacterium, Proteus, Bacterium, Cellulomonas, with gasifying bacteria such as Methanosarcina, Methanococcus and Methanobacterium. Seeds are domesticated by repeating batch type fermentations for two weeks under the same condition with the use of fractions highly containing paper of the same batch mentioned above. Calcium hydroxide slurry is used for adjusting pH of the slurry being fermented.

Figure 5:
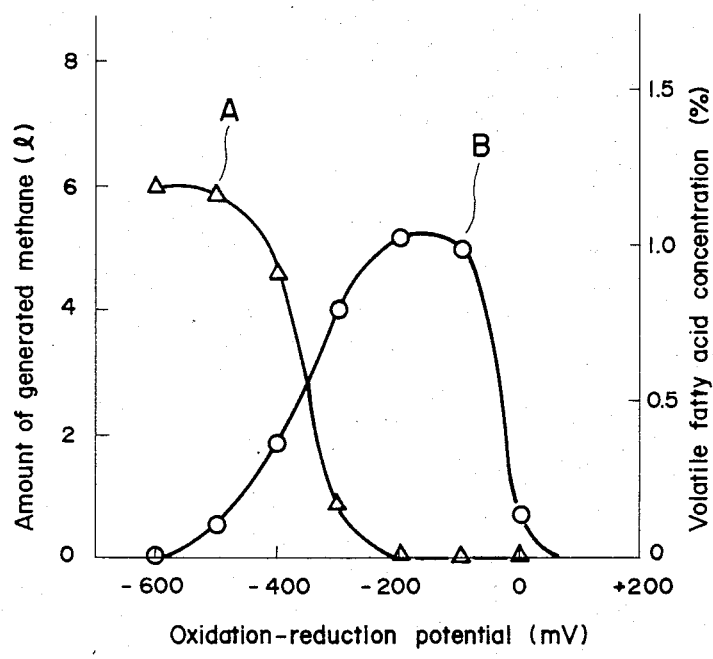
FIG. 5 shows the relation between the oxidation-reduction potential and the quantities of generated methane and produced volatile fatty acid in the embodiment.

The degree of digestion after the fifth day from the beginning of the present anaerobic digestion test is shown in FIG. 5. Symbol A represents produced amount of methane and symbol B represents concentration of volatile fatty acid.

It is clear from FIG. 5 that produced amount of methane A indicates that gasification proceeds only below −300 mV of oxidation-reduction potential and optimum region exists below −500 mV. On the other hand, it was confirmed that liquefaction efficiently proceeds in a weak reduction state below −50 mV and volatile fatty acid accumulates in the slurry. The reason why volatile fatty acid concentration decreases below −250 mV of oxidation-reduction potential is that volatile fatty acid is converted into methane.

It was determined from the results of the present embodiment that it is possible to achieve liquefaction only and to restrain gasification by maintaining the oxidation-reduction potential at −50–300 mV in the case of carrying out an anaerobic digestion process of wastes containing cellulose.

Embodiment 2

Figure 6:
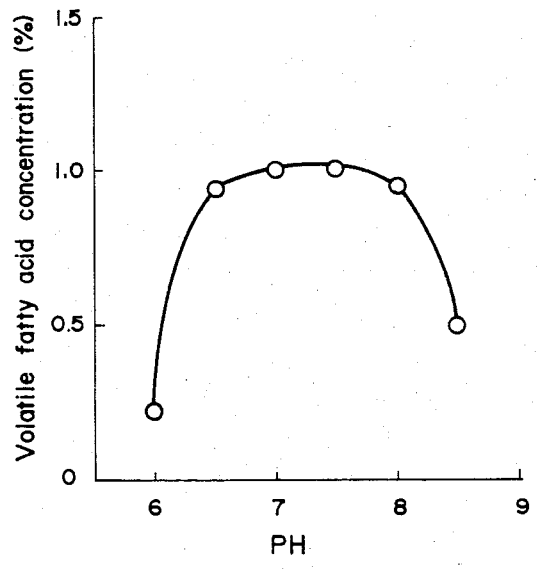
FIG. 6 is a diagram showing the relation between volatile fatty acid and pH in the embodiment.

Batch type liquefaction test was carried out with oxidation-reduction potential set at −200 mV and pH in the range of 6.0–8.5 definitely controlled by air blowing in the embodiment 1. The results obtained after five days is illustrated in FIG. 6. As apparent from FIG. 6, optimum pH range for liquefactive fermentation is between 6.5–8.0. Both in acidity side and in alkalinity side out of the above range, the fermentation starts late and production of fatty acid is extremely low.

Embodiment 3

Slurry is made by mixing 1 kg of the same fractions highly containing paper as those in the embodiment 1 and 9 kg of water and removing solid matters such as metals, glass, chinaware fragments, pebbles, etc., accumulated on the bottom of the container. Then, the said slurry of 2 kg/day was put into a cylindrical fermenting tank with effective volume of 12 l having an oxidation-reduction potential automatic controller, a turbine wing stirrer, a jacket for keeping warmth, and liquefaction was carried out successively under the conditions of oxidation-reduction potential −200 mV, stirring speed 150 rpm, temperature 60° C., pH 7.0 ($Ca(OH)_2$ slurry used) and the remaining period of four days. Oxidation-reduction potential was controlled by sending air into the fermenting tank with use of an oxygen supply pump interlocked with the oxidation-reduction potential controller and discharging it into slurry directly under the stirring turbine wings. By air blowing according to the present method, air bubbles were pulverized by shearing force of turbine wings to make the contacting area between oxygen and slurry large and to supply oxygen efficiently. As liquefying seeds, liquefied sludge obtained by liquefying the seeds used in the embodiment 1 under the above conditions for approximately two weeks was adopted. Liquefied slurry was taken out at the rate of 2 kg/day from the fermenting tank.

As a result of the present test, 0.041 kg/day of volatile fatty acids was produced. (Efficiency 0.4 kg/$kg^{VS}$) No methane was detected in the gas exhausted from the fermenting tank.

Embodiment 4

Slurry was made by mixing 1 kg of the same fractions highly containing paper as those in the embodiment 1 and water 11 kg and removing metals, glass, chinaware fragments pebbles on the bottom of the container. Then, 1.75 kg/day of the said slurry was put into a cylindrical fermenting tank with effective volume of 12 l having an oxidation-reduction potential controller, a gas lift type stirrer, a jacket for keeping warmth, an automatic pH controller and liquefaction was successively carried out under the conditions of oxidation-reduction potential −200 mV, temperature 60° C., pH 7.0 ($Ca(OH)_2$ slurry used) for four days. The oxidation-reduction potential was controlled by supplying air into the gas for stirring the fermenting tank with use of oxygen supply pump interlocked with the oxidation-reduction potential controller. The gas for stirring was repeatedly blown into the slurry, so, according to the present method, oxygen contained in the blown-in air is almost thoroughly utilized. As liquefying seeds, sludge obtained by liquefaction of the germs used in the embodiment 1 for two weeks under the same conditions. The slurry treated by liquefaction was taken out from the fermenting tank at the rate of 1.75 kg/day.

By this test, 0.03 kg/day of volatile fatty acid was produced (efficiency 0.4 kg/$kg^{VS}$). And no methane was detected in the gas exhausted from the fermenting tank.

Embodiment 5

According to the embodiment 3, 2.5 kg/day of liquefied slurry was obtained by successively liquefying 2.5 kg/day of slurry for the remaining period of three days. The said liquefied slurry contains 0.051 kg of volatile fatty acid and the produced amount of voltatile fatty acid to organic matters (VS) was 0.4 kg/$kg^{VS}$. No methane was detected in the gas exhausted from the fermenting tank.

Next, this liquefied slurry was put into the cylindrical gasifying and fermenting tank with effective volume of 26 l having a stirrer, a jacket for keeping warmth and an automatic pH controller. Gasifying fermentation was carried out under the conditions of stirring speed: 150 rpm, temperature: 60° C., pH: 7.4 (HCl solution used), remaining period: 9 days. As gasifying seeds, gasified sludge (digested sludge) obtained by repeated gasifications for approximately four weeks under the same conditions with the mixed gasifying bateria group of obligatory anaerobic gasifying bacteria such as Methanosarcina, Methanococcus, Methanobacterium was utilized. The digested slurry after gasifying fermentation was taken out once a day from the fermenting tank at the rate of 2.7 kg/day, remained for one day in a sedimentation separator of effecitve volume of 3 l and separated into gasified sludge (digested sludge) and supernatant liquid (separate water). 10% of the gasified sludge was returned to the gasifying fermenting tank as seeds and the rest was extracted out of the system as digested sludge. The gas produced by the fermentation was stored in the gas storage tank. The digesting rate obtained by reducing organic matters remaining in the digested sludge and separate water from the amount of put-in organic matters was 68%. The amount of generated gas in gasifying fermentation was 35.5 Nl being composed of methane 76% and carbon dioxide 24%. The amount of generated gas per 1 kg of put-in organic matters was 282 Nl.

The following effects are obtainable according to the present invention:

(1) Cellulose difficult to decompose can be decomposed in a short period because liquefaction proceeds efficiently, gasification being restrained in the anaerobic digestion of the wastes containing cellulose.

(2) Days required for disposing wastes containing cellulose can be substantially reduced by efficiently carrying out liquefaction and gasification in series.

(3) Digesting plant for the wastes containing cellulose can be of a small size because the disposing amount per unit area substantially increases by adopting the two-step digesting process.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What we claim is:

1. An anaerobic digestion process for wastes containing cellulose comprising the steps of:

(1) liquefying wastes containing cellulose in a slurry state by bringing said slurry into contact with facultative anaerobic bacteria, while adjusting the pH of said slurry to between 6.5 and 8.0 and controlling the oxidation-reduction potential of said slurry between −50 mV and −300 mV while supplying oxygen to said slurry, (2) converting the slurry obtained in the first step (1) into methane and carbon dioxide by bringing said slurry into contact with obligatory anaerobic bacteria without supplying oxygen to said slurry, and (3) separating the digested slurry obtained in the second step (2) into separate water and digested sludge.

2. The anaerobic digestion process of claim 1, wherein said facultative anaerobic bacterium is at least one member selected from the group consisting of Clostridium, Bacillus, Staphylacoccus, Proteus, Bacterium, Cellulomonas, Luminococcus, Butylivibrio and Bacteriodes.

3. The anaerobic digestion process of claim 1, wherein said obligatory anaerobic bacterium is at least one member selected from the group consisting of Methanosarcina, Methanococcus and Methanobacterium.

4. The anaerobic digestion process of claim 1, wherein a neutralizer is used to adjust the pH of said slurry to between 6.5 and 8.0, said neutralizer being at least one member selected from the group consisting of $NaOH$, $KOH$, $Na_2CO_3$, $Ca(OH)_2$ and $CaCO_3$.

* * * * *